United States Patent
Eckardt

(10) Patent No.: US 9,467,771 B2
(45) Date of Patent: Oct. 11, 2016

(54) BATTERY-POWERED WIRELESS AUDIO DEVICE AND A METHOD OF OPERATING SUCH A WIRELESS AUDIO DEVICE

(75) Inventor: Michael Eckardt, Stafa (CH)

(73) Assignee: SONOVA AG, Staefa (CH)

( * ) Notice: Subject to any disclaimer, the term of this patent is extended or adjusted under 35 U.S.C. 154(b) by 186 days.

(21) Appl. No.: 14/372,502

(22) PCT Filed: Jan. 18, 2012

(86) PCT No.: PCT/EP2012/050708
§ 371 (c)(1),
(2), (4) Date: Jul. 16, 2014

(87) PCT Pub. No.: WO2013/107507
PCT Pub. Date: Jul. 25, 2013

(65) Prior Publication Data
US 2014/0355781 A1 Dec. 4, 2014

(51) Int. Cl.
*H04R 1/10* (2006.01)
*H04R 25/00* (2006.01)
*H04W 52/02* (2009.01)
*A61N 1/36* (2006.01)

(52) U.S. Cl.
CPC .......... *H04R 1/1091* (2013.01); *H04R 1/1041* (2013.01); *H04R 25/305* (2013.01); *H04R 25/558* (2013.01); *H04W 52/0277* (2013.01); *A61N 1/36032* (2013.01); *H04R 25/43* (2013.01); *H04R 2201/109* (2013.01); *H04R 2225/61* (2013.01); *H04R 2460/03* (2013.01)

(58) Field of Classification Search
CPC H04R 1/1041; H04R 25/305; H04R 25/558; H04R 1/1091; H04R 2225/61; H04R 2460/03; H04R 25/43; H04R 2201/109; H04W 52/0277; A61N 1/36032

USPC .......... 381/312, 315, 329, 74; 713/320, 321, 713/323, 324, 340; 455/127.1–127.5
See application file for complete search history.

(56) References Cited

U.S. PATENT DOCUMENTS

| | | | |
|---|---|---|---|
| 5,721,783 A * | 2/1998 | Anderson | H04B 1/385 381/312 |
| 6,697,953 B1 | 2/2004 | Collins | |
| 7,650,519 B1 * | 1/2010 | Hobbs | G06F 1/266 713/300 |

(Continued)

OTHER PUBLICATIONS

International Search Report issued in Application No. PCT/EP2012/050708 dated Jul. 12, 2012.

(Continued)

Primary Examiner — David Ton
(74) Attorney, Agent, or Firm — Pearne & Gordon LLP

(57) ABSTRACT

A wireless audio device includes an audio streaming unit to wirelessly transmit an audio signal to a remote hearing device such as a hearing aid or a cochlear implant. A remote control unit to wirelessly controls the remote hearing device, a battery monitor determines a power level of a battery and provides a battery state signal indicative of the power level of the battery. A power management unit deactivates the audio streaming unit when the battery state signal reaches or falls below a first threshold and deactivates the remote control unit when the battery state signal reaches or falls below a second threshold, wherein the first threshold is higher than the second threshold. Also described is a method of operating such a wireless audio device as well as a hearing system including such a wireless audio device and a remote hearing device, such as a hearing aid or a cochlear implant.

15 Claims, 1 Drawing Sheet

(56) References Cited

U.S. PATENT DOCUMENTS

| | | | |
|---|---|---|---|
| 7,894,863 B2* | 2/2011 | Terai | H04M 1/6066 381/309 |
| 2008/0146292 A1 | 6/2008 | Gilmore | |
| 2011/0029799 A1* | 2/2011 | Walrath | G06F 1/26 713/340 |
| 2011/0185048 A1* | 7/2011 | Yew | H04M 1/72527 709/221 |
| 2011/0314185 A1* | 12/2011 | Conroy | G06F 1/3203 710/22 |

OTHER PUBLICATIONS

Written Opinion issued in Application No. PCT/EP2012/050708 dated Jul. 12, 2012.

* cited by examiner

BATTERY-POWERED WIRELESS AUDIO DEVICE AND A METHOD OF OPERATING SUCH A WIRELESS AUDIO DEVICE

TECHNICAL FIELD

The present invention pertains to a battery-powered wireless audio device capable of wirelessly transmitting an audio signal to a remote hearing device such as a hearing aid or a cochlear implant and of wirelessly controlling the remote hearing device. Furthermore, the present invention relates to a method of operating such a wireless audio device.

BACKGROUND OF THE INVENTION

Portable devices capable of audio streaming to headsets or earphones via a wireless link are becoming increasingly popular. An example of such a device is an audio player where the audio signal is transmitted over the air to a Bluetooth headset, thus avoiding the hassles of cable tangling or of the cable getting entwined with an object associated with a cable connection between the audio player and the headset.

Hearing aids (sometimes also referred to as hearing prostheses or hearing instruments) are small devices worn behind the ear or in the ear. They comprise one or more microphones, a processor, an amplifier and a miniature loudspeaker, commonly referred to as a receiver. The basic function of a hearing aid is the processing and the amplification of the acoustic signal arriving at the microphone(s) in order to compensate the hearing loss of the user.

Cochlear implants comprise one or more microphones, a processor, an amplifier and an output electrode which stimulates the nerve cells in the cochlear in order to compensate at least partially the hearing loss of a user.

The settings of a hearing aid or a cochlear implant may be modified by the user via a remote control unit.

In addition to the important basic functionalities users of hearing devices such as hearing aids or cochlear implants would also like to utilise audio streaming from an audio device as an alternative signal source. This has become possible with the availability of products like Phonak's iCom communication interface, Oticon's ConnectLine of devices, Siemens Tek, and Widex' DEX listening devices. Users of hearing devices such as hearing aids commonly also employ remote control units like for instance Phonak's PilotOne or Siemens' ProPocket. In order to minimise the number of devices that a hearing aid or cochlear implant user needs to carry around combined solutions like for example Oticon's Streamer providing both wireless audio streaming and remote control functionality within a single device have been developed.

In such a multifunction device the power consumption for wireless audio streaming is many times greater than that of the embedded remote control unit. The battery powering the device can typically only support wireless audio streaming for a few hours (e.g. 4 to 6). However, a user of a hearing aid or cochlear implant is accustomed to a remote control unit which can be operated continuously for many weeks employing the same battery. This leads to the problem that the battery of such a multifunction device is usually depleted after only a few hours of wireless audio streaming operation and thus also the remote control unit powered by the same battery can no longer be used until the battery has either been recharged or replaced by a new one. This is experienced as a great disadvantage of such multifunction devices by their users, since typically they are quite critically dependent on the remote control functionality to be operative in order for example to adjust the volume, switch to a different hearing program, select different settings or activate specific functions of the hearing device. On the other hand, not being able to continue wireless audio streaming when the battery is drained will normally be of less concern to the user.

SUMMARY OF THE INVENTION

It is an object of the present invention to overcome the above stated drawback present in known wireless audio devices including both an audio streaming as well as a remote control capability.

This object of the invention is achieved by a wireless audio device according to claim 1. Moreover, a hearing system comprising such a wireless audio device and a hearing device is provided.

It is a further object of the present invention to provide a method of operating such a wireless audio device that overcomes the above mentioned disadvantage.

This object of the invention is achieved by a method of operating a wireless audio device according to claim 9.

Specific embodiments of the present invention are given in the dependent claims.

The present invention provides a wireless audio device comprising:
- an audio streaming unit adapted to wirelessly transmit an audio signal to a remote hearing device;
- a remote control unit adapted to wirelessly control the remote hearing device;
- a battery monitoring unit adapted to determine a power level of a battery and to provide a battery state signal indicative of the power level of the battery; and
- a power management unit adapted to deactivate the audio streaming unit when the battery state signal reaches or falls below a first threshold and to deactivate the remote control unit when the battery state signal reaches or falls below a second threshold, wherein the first threshold is higher than the second threshold.

With such a wireless audio device it is possible to deactivate the audio streaming unit when the power level of the battery reaches or falls below a first predefined threshold. Once deactivated a unit consumes no or substantially less battery power that when the unit is active. Units performing less important functions can be deactivated in order to save battery power so that units carrying out more important functions are able to operate for a prolonged period of time than would be the case if all units were to remain active. Therefore, the remote control unit whose operation is more critical to the user is deactivated at a later time, when the battery state signal reaches or falls below a second predefined threshold, which is lower than the first predefined threshold, e.g. when the batter is close to being depleted.

For instance when such a wireless audio device is used in conjunction with a hearing aid audio streaming from the wireless audio device to the hearing aid can be stopped by deactivating the audio streaming unit when the power level of the battery is still high enough to support the operation of the remote control unit for an extended amount of time, thus ensuring that it remains possible to remotely control the hearing aid until the battery of the wireless audio device can be recharged or replaced with a new one, i.e. one that is at its full power level.

In an embodiment of the wireless audio device at least the first threshold is configurable.

In this way it is possible to define the power level of the battery at which the audio streaming unit is deactivated, thus allowing to choose the period of time during which audio streaming is allowed. The minimum value of the first threshold can for instance be limited to a certain amount above the value of the second threshold in order to ensure that the remote control unit can still be operated for a minimum amount time after the audio streaming unit has been deactivated. The second threshold value can for instance also be configured. The configuration of these thresholds can for example be performed via a programming interface that operationally connects the wireless audio device with an external programming device either via a cable or wirelessly.

In a further embodiment of the wireless audio device at least the first threshold can be set via an input means located at the wireless audio device.

This for instance allows the user of the wireless audio device to change the value of the first threshold according to his current needs. For example if a replacement battery is at hand, the user can set the first threshold to a low value, since the battery can be immediately replaced once the audio streaming unit has been deactivated, and it is therefore adequate to have only a short extra runtime for the remote control unit after deactivation of the audio streaming unit.

In a further embodiment of the wireless audio device at least the first threshold is automatically determinable by the wireless audio device itself dependent on the type of the battery being used to power the wireless audio device.

Such an automatic determination of the first threshold can for instance be based on a look-up table comprising a list of battery types with associated first thresholds, where information regarding the battery type can for example be provided to the wireless audio device via an input means or configured via a programming interface. Alternatively, the battery type can for instance be automatically determined by the wireless audio device itself based on measurements, e.g. using the battery monitoring unit, of the battery's peak power level and/or its discharge properties, which especially allows to distinguish between rechargeable and non-rechargable batteries or between batteries employing different technologies, i.e. different battery chemistries.

In a further embodiment the wireless audio device further comprises a logging means adapted to log and store information related to the battery state signal as a function of time.

In this way it is possible to monitor the discharge characteristics of the battery being used and then to exploit this information, e.g. to optimise the first and second thresholds or to help determine the power consumption of various units, and based thereupon to calculate estimates of the remaining runtime for the various units such as the audio streaming unit or the remote control unit.

In a further embodiment the wireless audio device further comprises an estimation unit adapted to determine an estimate of an amount of time remaining until the audio streaming unit is deactivated, wherein the estimate is determined based on the battery state signal, more particularly based on the information logged by the logging means.

Based on this information the user can plan ahead and take appropriate action, e.g. recharge the battery early on, so that the battery is at a sufficient power level to sustain audio streaming operation for a desired amount of time. Moreover, the user is kept aware of the amount of time during which the remote control unit can still be used.

In a further embodiment the wireless audio device further comprises a display means adapted to display to a person the battery state signal and/or the estimate of the amount of time remaining until the audio streaming unit is deactivated.

The wireless audio device can be part of a hearing system comprising a remote hearing device, the remote hearing device being a hearing device adapted to be worn at an ear of an individual, more particularly the remote hearing device being one of the following:
   a hearing aid,
   a cochlear implant,
   an in-ear receiver,
   an in-ear monitor,
   an earphone,
   a headset.

The hearing aid may be of the behind-the-ear (BTE), in-the-ear (ITE), in-the-canal (ITC) or completely-in-canal (CIC) type.

Furthermore, the present invention provides a method of operating a wireless audio device comprising an audio streaming unit for wirelessly transmitting an audio signal to a remote hearing device and a remote control unit for wirelessly controlling the remote hearing device, the wireless audio device being powered by a battery, the method comprising the steps of:
   determining a power level of the battery;
   providing a battery state signal indicative of the power level of the battery;
   deactivating the audio streaming unit when the battery state signal reaches or falls below a first threshold; and
   deactivating the remote control unit when the battery state signal reaches or falls below a second threshold,
wherein the first threshold is higher than the second threshold.

In an embodiment the method further comprises the step of configuring the wireless audio device with data pertaining to at least the first threshold.

In a further embodiment the method further comprises the step of setting at least the first threshold via an adjustment means located at the wireless audio device.

In a further embodiment the method further comprises the step of automatically determining by the wireless audio device itself of data pertaining to at least the first threshold dependent on the type of the battery being used to power the wireless audio device.

In a further embodiment the method further comprises the step of logging information related to the battery state signal.

In a further embodiment the method further comprises the step of estimating an amount of time remaining until the audio streaming unit is deactivated, wherein the estimate is determined based on the battery state signal, more particularly based on the logged information related to the battery state signal.

In a further embodiment the method further comprises the step of displaying to a person the battery state signal and/or the estimate of the amount of time remaining until the audio streaming unit is deactivated.

It is pointed out that further combinations of the above-mentioned embodiments may be employed to realise a more specific configuration according to the present invention.

BRIEF DESCRIPTION OF THE DRAWINGS

The present invention is further described in the following with reference to the accompanying drawings, where.

DETAILED DESCRIPTION OF THE INVENTION

Figure 1:
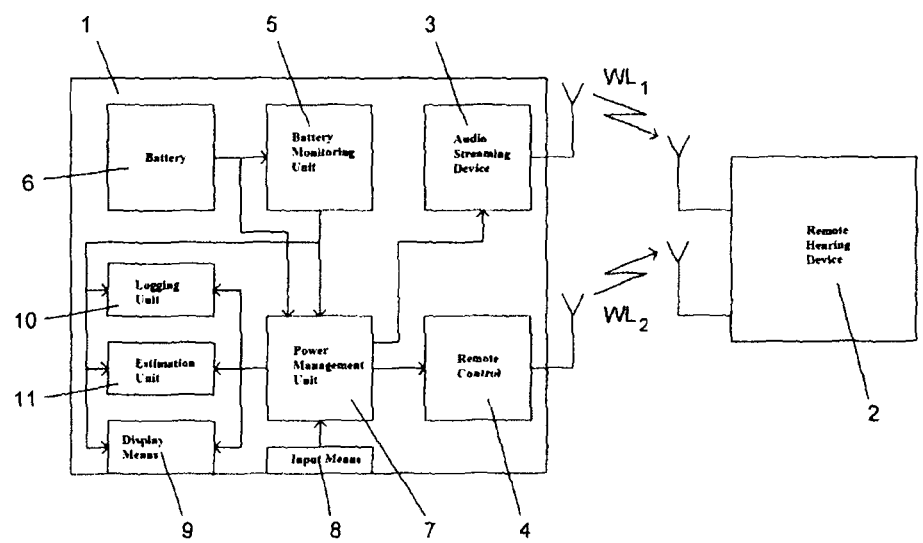
FIG. 1 depicts in a schematic representation in the form of a block diagram a wireless audio device according to the present invention.

FIG. 1 shows the block diagram of an exemplary embodiment a wireless audio device 1 according to the present invention. The wireless audio device 1 is operationally connected to a remote hearing device 2 such as a hearing aid or a cochlear implant. Both devices 1 and 2 together form a hearing system, wherein the wireless audio device 1 is regarded as an accessory to the hearing device 2, e.g. a hearing aid or a cochlear implant, which provides the primary function to the user, e.g. that of compensating the user's hearing deficiency, whereas the wireless audio device 1 provides auxiliary functions, namely primarily a remote control function and secondarily an audio streaming function. The wireless audio device 1 therefore comprises both an audio streaming unit 3 and a remote control unit 4. The audio streaming unit 3 transmits an audio signal to the remote hearing device 2 via a first wireless link $WL_1$, and the remote control unit 4 transmits a control signal to the remote hearing device 2 via a second wireless link $WL_2$. The first and second wireless link $WL_1$, $WL_2$ can be completely independent, e.g. operate in different frequency bands, or they can both employ the same frequency band and be assigned to different logical channels, e.g. a transport channel and a control channel, having different duty-cycles. Moreover, the transceiver hardware for transmitting and receiving signals over the first and second wireless link $WL_1$, $WL_2$ may be separate for each wireless link $WL_1$, $WL_2$ (e.g. two radios in both the wireless audio device 1 and the remote hearing device 2) or shared to handle both wireless links $WL_1$, $WL_2$ (e.g. only a single radio in the wireless audio device 1 and the remote hearing device 2). The audio signal transmitted by the audio streaming unit 3 is received by the remote hearing device 2, e.g. a hearing aid which outputs the audio signal via a miniature loudspeaker, typically after applying signal processing, e.g. frequency-dependent amplification, to the audio signal in order to improve the hearing capability of the user of the hearing aid. On the other hand the control signal sent by the remote control unit 4 is received by the remote hearing device 2 where it for instance switches the mode of operation of the remote hearing device 2. In the case of the remote hearing device 2 being a hearing aid, the remote control unit 4 can select a different hearing program or function, e.g. can be switched from an audio streaming program, where the audio signal from the audio streaming unit 1 is applied to the loudspeaker, to a speech-in-noise program, where the sound picked-up by one or more microphones of the hearing aid is processed by a signal processing unit in the hearing aid to reduce the noise and subsequently output by the loudspeaker. The remote control can for example also control the volume of the audio signal output by the loudspeaker.

A battery 6 supplies power to the units within the wireless audio device 1. The battery 6 is connected directly to a power management unit 7, which distributes the battery power to the individual units. Alternatively, the battery can be directly connected to all the units and the power management unit 7 merely activates and deactivates the individual units. In the latter case, when a unit is deactivated it consumes no battery power or at least considerably less battery power than when the unit is active. The battery 6 is also connected to a battery monitoring unit 5 which determines the power level of the battery 6 and provides a battery state signal indicative of the power level of the battery 6 to the power management unit 7. Furthermore, the battery state signal is also provided to a display means 9, which presents an indication of the power level of the battery 6 to a person. Based on the battery state signal the power management unit 7 determines whether it is necessary to deactivate a unit. The power management unit 7 will deactivate the audio streaming unit 3 as soon as a first threshold TH1 of the power level of the battery 6 is reached and the audio streaming unit 3 is kept deactivated as long as the power level of the battery 6 remains below the first threshold TH1. Likewise, the power management unit 7 will deactivate the remote control unit 4 as soon as a second threshold TH2 of the power level of the battery 6 is reached.

Figure 2:
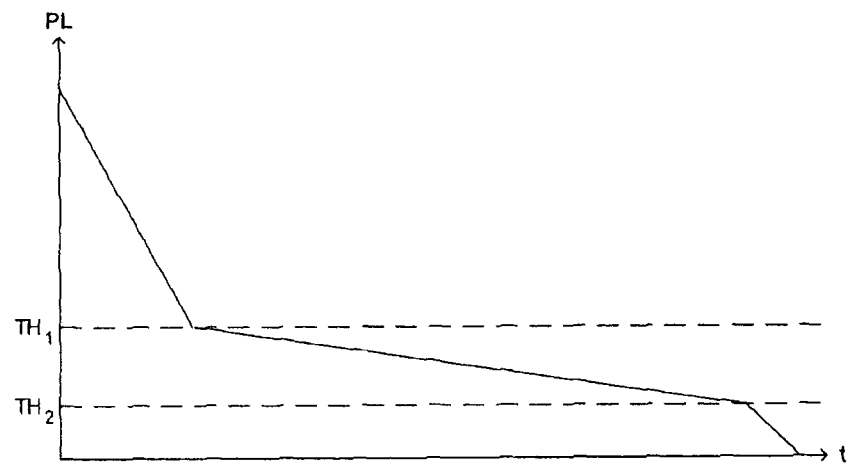
FIG. 2 shows a graphical representation of the power level of a battery as a function of time.

FIG. 2 illustrates a graph of the power level PL of the battery 6 over a complete discharge cycle. In the depicted example, the audio streaming device 3 is initially active from the point where the battery 6 is at its fully power level until the power level of the battery 6 has reached the first threshold $TH_1$, whereupon the audio streaming device 3 is deactivated. The high power consumption of the audio streaming device 3 when it is active and operational is apparent from the step slop of the power level trace, i.e. the rapid decline of the power level of the battery 6 over time t during this phase. Subsequently, when only the remote control unit 4 is active, the course of the power level is much less steep, so that the remote control unit 4 can operate for a prolonged period of time until the second threshold $TH_2$ is reached, whereupon the remote control unit 4 is also deactivated.

As is further depicted in FIG. 1, the first and second threshold $TH_1$, $TH_2$ can be set manually by a user via an input means 8, e.g. keys, a control knob or a rotary switch, located at the wireless audio device 1. Alternatively, the thresholds $TH_1$, $TH_2$ can be configured via a wired or wireless configuration/programming interface from a separate configuration/programming device via an appropriate configuration/programming interface at the wireless audio device 1 (both not shown in FIG. 1). In a further alternative, the thresholds $TH_1$, $TH_2$ may be automatically determined by wireless audio device 1 itself based on data provided to the wireless audio device 1 regarding the type of battery being used to power the wireless audio device 1. Moreover, the thresholds $TH_1$, $TH_2$ can be automatically determined by the wireless audio device 1 itself based on measurements performed for instance by the battery monitoring unit 5 and/or measurement data logged by the logging unit 10.

From such data the discharge characteristics of the battery 6 being used to power the wireless audio device 1 can be determined, and based thereupon the type of battery 6 in use can be identified.

As mentioned above a logging unit 10 is provided in the wireless audio device 1 in order to save and store values of the battery state signal over time allowing for instance subsequent analysis of the discharge behaviour of the battery 6, which in turn provides information regarding the usage and operation of the wireless audio device 1 by the specific user.

Such information can be utilised in the estimation unit 11, which is capable of determining an estimate of an amount of time remaining until the audio streaming unit 3 and/or the remote control unit 4 is deactivated.

Information regarding the battery state signal, i.e. indicating the presently remaining power level of the battery 6 is displayed to a user via a display means 9 such as an LED indicator, an LCD display or a screen. Furthermore, estimates of the time remaining until a unit is deactivated can be brought to the attention of a user via a numerical display.

What is claimed is:

1. A wireless audio device comprising:
an audio streaming unit;
a remote control unit; and
a battery;
wherein:
the audio streaming unit wirelessly transmits an audio signal to a remote hearing device;
the remote control unit wirelessly controls the remote hearing device;
the battery supplies power to units and devices within the wireless audio device;
a power level of the battery is monitored to provide a battery state signal;
when the battery state signal reaches or falls below a first threshold the audio streaming unit is deactivated; and
when the battery state signal reaches or falls below a second threshold that is lower than the first threshold the remote control unit is deactivated.

2. The wireless audio device of claim 1, wherein at least the first threshold is configurable.

3. The wireless audio device of claim 1, wherein at least the first threshold is settable by an input means located at the wireless audio device.

4. The wireless audio device claim 1, wherein at least the first threshold is automatically determinable by the wireless audio device dependent on the type of the battery.

5. The wireless audio device of claim 1, further comprising a log, wherein the log logs information related to the battery state signal.

6. The wireless audio device of claim 5 wherein an amount of time remaining until the audio streaming unit is deactivated is estimated; and wherein the estimate is determined based on the battery state signal, more particularly based on the information logged by the log.

7. The wireless audio device of claim 1, further comprising a display means, wherein the display means displays the battery state signal and/or the estimate of the amount of time remaining until the audio streaming unit is deactivated.

8. A hearing system comprising a wireless audio device according to claim 1 and a remote hearing device, the remote hearing device being a hearing device adapted to be worn at an ear of an individual, more particularly the remote hearing device being one of the following:
a hearing aid,
a cochlear implant,
an in-ear receiver,
an in-ear monitor,
an earphone,
a headset.

9. A method of operating a wireless audio device having an audio streaming unit for wirelessly transmitting an audio signal to a remote hearing device and a remote control for wirelessly controlling the remote hearing device wherein the wireless audio device is powered by a battery, the method comprising the steps of:
determining a power level of the battery;
providing a battery state signal indicative of the power level of the battery;
deactivating the audio streaming unit when the battery state signal reaches or falls below a first threshold; and
deactivating the remote control when the battery state signal reaches or falls below a second threshold,
wherein the first threshold is higher than the second threshold.

10. The method of claim 9, further comprising the step of configuring the wireless audio device with data pertaining to at least the first threshold.

11. The method of claim 9, further comprising the step of setting at least the first threshold via an input means located at the wireless audio device.

12. The method of claim 9, further comprising the step of automatically determining by the wireless audio device of data pertaining to at least the first threshold dependent on the type of the battery.

13. The method of claim 9, further comprising the step of logging information related to the battery state signal.

14. The method of claim 13, further comprising the step of estimating an amount of time remaining until the audio streaming unit is deactivated, wherein the estimate is determined based on the battery state signal, more particularly based on the logged information.

15. The method of claim 9, further comprising the step of displaying the battery state signal and/or the estimate of the amount of time remaining until the audio streaming unit is deactivated.

* * * * *